United States Patent [19]

Bron et al.

[11] Patent Number: 5,049,694

[45] Date of Patent: Sep. 17, 1991

[54] PHARMACEUTICAL COMPOSITION HAVING RELAXING ACTIVITY WHICH CONTAINS A NITRATE ESTER AS ACTIVE SUBSTANCE

[75] Inventors: Jan Bron, Giessenburg; Geert J. Sterk, Utrecht; Jan F. van der Werf, Amsterdam-Z.O.; Hendrik Timmerman, Voorschoten, all of Netherlands

[73] Assignee: Cedona Pharmaceuticals B.V., Haarlem, Netherlands

[21] Appl. No.: 407,355

[22] Filed: Sep. 14, 1989

[30] Foreign Application Priority Data

Sep. 15, 1988 [NL] Netherlands .......................... 8802276

[51] Int. Cl.$^5$ ............................................. C07C 77/02
[52] U.S. Cl. .................................. 558/480; 558/484; 558/482; 558/486; 558/488
[58] Field of Search ............... 558/480, 458, 444, 482, 558/483, 484, 485, 486, 487, 488; 514/506

[56] References Cited

U.S. PATENT DOCUMENTS

| | | | |
|---|---|---|---|
| 3,301,891 | 1/1967 | Schickh et al. | 558/480 |
| 3,428,667 | 2/1969 | Hamel et al. | 558/483 |
| 3,853,891 | 12/1974 | Simpson | 546/244 |
| 4,336,408 | 6/1982 | Barnes | 568/853 |
| 4,417,903 | 11/1983 | Hinkamp | 44/53 X |
| 4,479,905 | 10/1984 | Knapp et al. | 558/483 |
| 4,801,596 | 1/1989 | Simon et al. | 514/327 X |
| 4,863,949 | 9/1989 | Simon et al. | 548/483 X |

*Primary Examiner*—Robert L. Stoll
*Assistant Examiner*—Chhaya Sayala
*Attorney, Agent, or Firm*—Burgess, Ryan & Wayne

[57] ABSTRACT

The invention relates to pharmaceutical compositions containing novel nitrate esters, of which it was found that they are useful for the treatment of ischemiatic heart diseases, decompensatio cordis, myocardial infarction and hypertension.

11 Claims, No Drawings

PHARMACEUTICAL COMPOSITION HAVING RELAXING ACTIVITY WHICH CONTAINS A NITRATE ESTER AS ACTIVE SUBSTANCE

The invention relates to a pharmaceutical composition having relaxing activity, for example for the treatment of heart and vascular diseases, which contains a nitrate ester as active substance.

It was now found that a series of novel organic nitrate esters to be further described, are e.g. useful as therapeutical composition for example for the treatment of ischemiatic heart diseases (such as angina pectoris and silent ischaemia), decompensatio cordis, myocardial infarction, hypertension (in particular portal hypertension), achalasia, tardy dyskinesia, etc.

For decades organic nitrate esters such as glyceryl trinitrate and isosorbide dinitrate have been used therapeutically, in particular for the treatment of angina pectoris and decompensatio cordis. Owing to their vasodilatory activity they diminish especially the preload of the heart; the post-load is also affected, be it to a lower extent. The net result is a lower need of oxygen to the heart, that meets a lower resistance in pumping owing to the influence of glyceryl trinitrate or isosorbide dinitrate.

A clinically described problem in the therapeutical use of organic nitrate esters, such as glyceryl trinitrate and isosorbide nitrate, is the development of so-called tolerance by chronical administration.

Consequently there is need of view vasodilatory nitrate esters of a chemical structure differing from simple and therefore possibly non-selective active nitrate esters such as glyceryl trinitrate and isosorbide dinitrate, which are to be preferred in selective therapeutical treatment of inter alia ischaemiatic heart diseases. Such organic nitrate esters different from glyceryl trinitrate and isosorbide dinitrate have been described. For example patent applications EP 83107232.7, EP 8611080.8 and EP 85305471.6 describe respectively pyridylalkyl nitrates, nitrate esters of 2- c.p. 3-alkanol-1,4-benzodioxane derivatives and nitrate esters of N-alkanol-phthalimide derivatives. All these patent applications relate to relaxing or hypertensive compounds. However, the compounds described in these patent applications usually show in-vitro activity exceeding the activity of isosorbide dinitrate let alone approach that of glyceryl trinitrate. The present invention relates to noel, organic nitrate esters. Quite a part of said novel organic nitrate esters is more active in vitro than isosorbide dinitrate, and a number of compounds show a larger relaxing activity in vitro than glyceryl trinitrate.

The novel nitrate ester

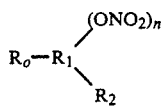

, wherein $R_0$ represents H, OH which may be esterified by substituted or unsubstituted aliphatic or (hetero)aromatic carboxylic acid, or a group

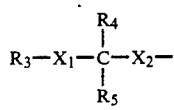

, in which latter formula $R_3$ represents H or a substituted or unsubstituted (hetero)aromatic group, but is possibly lacking in class $X_2$ represents a triple bond, $R_4$ represents H, OH or straight or branched alkyl, alkenyl, alkynyl or alkoxy or cyclopropyl, or is identical to $R_3$, but is possibly lacking in case $X_2$ represents a triple bond, $R_5$ represents H or straight or branched alkyl, but is lacking the case $X_2$ represents a double or triple bond, $X_1$ represents a single bond, methylene, a substituted or unsubstituted carboxamide group or amino group, O or S, but is lacking in case $X_2$ represents a triple bond and $X_2$ represents a single bond, a double bond (in which case $R_5$ is then lacking), or a triple bond (in which case $R_5$ and either $R_3$—X, or $R_4$ are then lacking), a substituted or unsubstituted carboxamide group or amino group, O or S, $R_1$ represents straight or branched alkylene having 1-8 carbon atoms in a straight chain, cycloalkylene having 3-7 carbon atoms, bicycloalkylene having 5-12 carbon atoms, a 1,4:3,6-dianhydrohexitolylene group or a derivative from said group, or mono-, di- or tri-alkylene substituted cycloalkylene, $R_2$ represents H, OH, straight or branched alkyl or alkylphenyl, where phenyl has the same substitution possibilities as $R_3$, or substituted or unsubstituted thioxanethenyl, substituted or unsubstituted benzocycloalkanyl having 5-7 carbon atoms in the cycloalkanyl chain, substituted or unsubstituted benzocycloalkenyl having 5-7 carbon atoms in the cycloalkenyl chain, substituted or unsubstituted dibenzocycloalkanyl having 5-7 carbon atoms in the cycloalkanyl chain, or substituted or unsubstituted dibenzocycloalkenyl having 5-7 carbon atoms in the cycloalkyl chain and n is 1, 2 or 3. The invention also covers the salts derived from such an ester.

The invention has the characterizing features that in the pharmaceutical composition containing a nitrate ester as defined in the preamble, said ester is

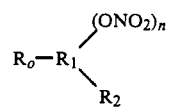

,
or is a salt derived from such an ester.

The pharmaceutical compositions of the invention are of the kind ordinarily used, such as tablets, capsules and solutions for oral administration, suppositoria, sterile solutions and suspensions for parenteral administrations and compositions for transdermal administration.

Pharmaceutical compositions contain a compound in an amount to deliver 0.001-10 mg/kg. The pharmaceutical compositions may also contain acceptable pharmaceutical adjuvants in order to manufacture said pharmaceutical compositions according to technically known processes. The pharmaceutical compositions comprise solid and semi-solid dosage forms such as tablets, hard gelatin capsules, soft gelatin capsules and suppositories, coated and/or uncoated if applicable (containing 0.05-1,000 mg per single dosage form), liquid dosage forms such as oral or parenteral solutions and eye drops, transdermal dosage forms such as patches (containing 0.05-1,000 mg per single dosage form) and ointments.

Typical dosage forms include tablets, capsules, pills, bulk powders, elixirs, solutions, suspensions, syrups, suppositories or ointments, creams and the like for topical administration.

Preferably, the nitrate ester is combined with any suitable nontoxic pharmaceutically acceptable inert carrier material. Such carrier materials are well known to those skilled in the art of pharmaceutical formulations. In a typical preparation for oral administration, e.g., tablet or capsule, the active substance in an effective amount is combined with any oral nontoxic pharmaceutically acceptable insert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate. If desired, a conventional pharmaceutically acceptable dye can be incorporated into the dosage unit form, i.e., any of the standard FD and C dyes. Sweetening and flavoring agents and preservatives can also be included, particularly when a liquid dosage form is formulated, e.g., an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. Such compositions should preferably contain at least 0.1% of active components; generally, the active ingredients will be between about 2% to about 90% of the weight of the unit.

The composition of the present invention may also be formulated for intramuscular, subcutaneous, rectal, dermal or topical use by known methods.

$R_o$ or $R_3$ represents an aromatic group e.g. phenyl, pyridyl, thienyl, furanyl, thiazolyl, naphthyl, indolyl, chinolyl, etc. Substituents to the aromatic group are for example halogen (F, Cl, Br), straight or branched, and substituted or unsubstituted alkyl (for example methyl, ethyl, n-propyl, i-propyl, t-butyl, trifluoromethyl, etc.), straight or branched alkoxy (for example methoxy, ethoxy, propoxy, i-butoxy) or alkylthio, straight or branched alkenyl or alkynyl, nitro, cyano, dialkylamino, sulfamoyl, hydroxyl, carboxyl, carboxamide, alkoxycarbonyl, nitroxyalkyl, etc. Substituents to $R_3$ may also be identical to $R_3$.

In $R_2$, $R_4$ and $R_5$ alkyl is for example methyl, ethyl, n-propyl, i-propyl, t-butyl, etc.

In $R_2$ alkylphenyl is for example benzyl, ethylphenyl, propylphenyl, etc. and in $R_4$ alkoxy is for example methoxy, ethoxy, propoxy, etc.

Synthesis

Esters of nitric acid may be prepared using one of the following reagents and methods such as for example described in the mentioned literature references:
1. Mixture of nitric acid and sulphuric acid (Boschan R., Merrow R. T., Dolah R. W., Chem. Rev. 1955; 55, 485);
2. Nitronium tetrafluoroborate (Olah G., Noszko L., Kuhn S., Szelke M., Chem. Ber. 1956; 89, 2374);
3. Thionylchloride/silvernitrate (Hakimelahi G. H., Sharghi H., Zarrimmayeh H., Khalafi-Nezhad A., Helv. Chim. Act. 1984; 67, 906);
4. Acetylnitrate (Snatzke G., Laurent H., Wiechert R., Tetrahedron 1969; 25, 761),
5. N-nitrocollidinium tetrafluoroborate (Olah G. a., Narang S. C., Pearsons R. L., Cupas C. A., Synthesis 1978; 452).
6. Alkylhalogenide with silver- or mercury nitrate (Fieser L. F., Doering W. von E., J. Am. Chem. Soc. 1946; 68; 2252; Mc Killop A., Ford M. E., Tetrahedron 1974; 30, 2467).

The compounds of this invention can be prepared with the above reagents and by means of the methods described in the literature. Preferably reagents and methods according to 2, 4, 5 and 6 are applied.

In a standard recipe 22 mmole of nitric acid dissolved in 5 ml of acetic acid is added to a solution of 20 mmole of an alcohol (respectively 10 mmole of a diol respectively 6.5 mmol of a triol) in 50 ml of ethylacetate at 0° C. under nitrogen, followed by addition of 5 ml of acetic anhydride. After 20 h at room temperature the reaction mixture is washed with a saturated solution of bicarbonate. The organic layer is dried and concentrated by evaporation. The residue is purified by means of column chromatography (silica gel) by elution with a mixture of petroleum ether (60-80) and diethylether). The yield varied from 30 to 98%. The purity and identity of the compounds was established by means of thin layer chromatography (silica gel with fluroscence indicator respectively detection after spraying with a solution of 1% diphenylamine in sulphuric acid), nuclear magnetic resonance (Bruker WH 90; using tetramethylsilane as intern standard) and mass spectrometry (Finnigan MAT 90, double focussing mass spectrometer with reversed geometry (BE).

Pharmacology

The relaxing potency of the compounds as described is tested in vitro on contracted strips of the rats' arota. Male Wistar rates (200–220 g) are killed by decapitation. The thoracal aorta is removed and is helically cut into strips (length: ±10 mm, width: ±2 mm; 4 strips per rat).

The strips are suspended in organ baths filled with 20 ml of Krebs' medium with a constant temperature of 37° C. passing through $O_2/CO_2$ (95/5) and subsequently for 2 h equilibrated under an isotonic load of 500 mg. The medium is renewed every 20 minutes.

After equilibration contraction takes place by addition of $10^{-7M}$ phenylefrine to the medium. After reaching the maximal contraction the composition with the organic nitrate ester to be tested in cumulative concentration steps is relaxed.

The degree of relaxation is expressed as a percentage of the maximal contraction (=100%) reached with $10^{-7}$ M phenylefrine. The relaxing potency of the tested compounds is expressed as the $EC_{50}$: the concentration with which relaxation took place up to 50% of the contraction induced by $10^{-7}$ M phenylefrine. From a number of compounds the $EC_{50}$-values have been stated in Table 1. For comparison the $EC_{50}$-values of glyceryltrinitrate and isosorbidedinitrate have also been included.

EXAMPLES

The sequential numbering used for the hereafter mentioned examples is again used in the further description following these examples to specify the said compounds.

1. 2-phenylethanol nitrate;
2. 3-phenyl-1-propanol nitrate;
3. 4-phenyl-1-butanol nitrate;
4. 2-(4-methylphenyl)ethanol nitrate;
5. 2-(2-nitrophenyl)ethanol nitrate;
6. 3-(4-methoxyphenyl)-1-propanol nitrate;
7. 2-phenyl-2-methyl-1-propanol nitrate;
8. 2-(4-chlorophenyl)-2-methyl-1-propanol nitrate;
9. 2-(1-naphthyl)ethanol nitrate;
10. 2-(2-naphthyl)-1,3-propanediol nitrate;
11. 1,4-bis(2-(nitroxyethyl)benzene;
12. 1,4-bis(2-nitroxyethyl)-2,3,5,6-tetramethylbenzene;
13. 2,2-diphenyl-1-ethanol nitrate;
14. 3,3-diphenyl-1-propanol nitrate;
15. 1,1-diphenyl-2-propanol nitrate;
16. 4,4-di-(4-fluorophenyl)-2-butanol nitrate;
17. 2-(5H-dibenzo[a,d]cycloheptene-5-yl)ethanol nitrate;
18. 2-(2-chlorothioxanthene-10-yl)ethanol nitrate;
19. 10,11-dihydro-5H-dibenzo[a,d]cycloheptene-5-ylmethanol nitrate;
20. 2-diphenylmethyl-1,3-propanediol dinitrate;
21. 3-phenyl-3-(4-pyridyl)-1-propanol nitrate-4-methylbenzenesulfonate;
22. 2-(3-thienyl)ethanol nitrate;
23. 1,3-diphenyl-2-propanol nitrate;
24. 1,3-dibenzyloxy-2-propanol nitrate;
25. 2-diphenylmethoxyethanol nitrate;
26. 2-(α-(4-chlorophenyl)-4-t.butylbenzyloxy)ethanol nitrate;
27. 2-(α-(4-chlorophenyl)-4-t.butylbenzyl)-1,4:3,6-dianhydroglucitol nitrate;
28. 2-diphenylmethyl-1,4:3,6-dianhydroglucitol nitrate;
29. 2-(4-chloro-α-(2-chloro-5-thienyl)benzyl)-1,4:3,6-dianhydroglucitol nitrate;
30. 2-(2-thienyl)ethanol nitrate;
31. 1-phenyl-1-nitroxymethylcyclopropane;
32. 3-phenoxy-1,2-propanediol dinitrate;
33. 6-acetyloxy-1-hexanol nitrate;
34. 1,6-dihydroxybicyclo[4,4,0]decyl dinitrate;
35. 1,4-cyclohexanediol dinitrate;
36. 1,4-di(hydroxymethyl)cyclohexane dinitrate;
37. 1,2-cyclohexanediol dinitrate;
38. 1,5-pentanediol dinitrate;
39. 1,3-cyclohexanediol dinitrate;
40. 2-hydroxy-1-cyclohexanol nitrate;
41. 2-ethyl-2-n.butyl-1,3-propanediol dinitrate;
42. 1,12-dodecanediol dinitrate;
43. 1,6-hexanediol dinitrate.

Experimentally

Synthesis

The nitrate esters mentioned below can be prepared with the above mentioned methods.

2-Phenylethanol nitrate (1)

Starting from 2-phenylethanol.
Melting point: (oil)
TLC: Rf=0.68 (diethylether:petroleumether 60-80/(1:1)
$^1$H-NMR(CDCl$_3$): 3.00 ppm, triplet, J=7.2 Hz, 2.0 H (phenyl—CH$_2$); 4.60 ppm, triplet, J=7.2 Hz, 2.0 H(CH$_2$—O); 7.06-7.44 ppm, multiplet, 5.0 H (aromatic H).

3-phenyl-1-propanol nitrate (2)

Starting from 3-phenyl-1-propanol.
Melting point: (oil)
TLC: Rf=0.75 (diethylether:petroleumether 60-80/1:3)
$^1$H-NMR(CDCl$_3$): 2.04 ppm, quintet, J=6.3 Hz, 2.0 H (C—CH$_2$—C); 2.70 ppm, triplet, J=7.2 Hz, 2.0 H (phenyl—CH$_2$); 4.44 ppm, triplet, J=6.3 Hz, 2.0 H (CH$_2$—O); 7.06-7.40 ppm, multiplet, 5.0 H (aromatic H).

4-phenyl-1-butanol nitrate (3)

Starting from 4-phenyl-1-butanol.
Melting point: (oil)
TLC: Rf=0.80 (ethylacetate:petroleumether 60-80/1:3)
$^1$H-NMR(CDCl$_3$): 1.44-1.96 ppm, multiplet, 4.0 H (C—CH$_2$—CH$_2$—C); 2.40-2.80 ppm, multiplet, 2.0 H (phenyl—CH$_2$); 4.22-4.56 ppm, multiplet, 2.0 H (CH$_2$O): 6.92-7.42 ppm, multiplet, 5.0 H (aromatic H).

2-(4-methylphenyl)ethanol nitrate (4)

Starting from 2-(4-methylphenyl)ethanol.
Melting point: (oil)
TLC: Rf=0.71 (diethylether:petroleumether 60-80/1:5)
$^1$H-NMR (CDCl$_3$): 2.34 ppm, singlet, 3.0 H (CH$_3$); 2.98 ppm, triplet, J=7.0 Hz, 2.0 H (phenyl—CH$_2$); 4.60 ppm, triplet J=7.0 Hz, 2.0 H (CH$_2$—O); 7.10 ppm, singlet, 4.0 H (phenyl-H)

2-(2-nitrophenyl)ethanol nitrate (5)

Starting from 2-(2-nitrophenyl)ethanol.
Melting point: (oil)
TLC: Rf=0.57 (eluant:diethylether:petroleumether 60-80/1:2)
$^1$H-NMR(CDCl$_3$): 3.29 ppm, triplet, J=6.3 Hz, 2.0 H (phenyl—CH$_2$); 4.75 ppm, triplet, J=6.3 Hz, 2.0 H (CH$_2$—O); 7.25-7.68 ppm, multiplet, 4.0 H (aromatic H$_4$, H$_5$ and H$_6$); 7.86-8.10 ppm, multiplet, 1.0 H (aromatic H$_3$)

3-(4-methoxyphenyl)-1-propanol nitrate (6)

Starting from 3-(4-methoxyphenyl)-1-propanol.
Melting point: (oil)
TLC: Rf=0.54 (diethylether:petroleumether 60-80/1:5)
$^1$H-NMR(CDCl$_3$): 1.79-2.19 ppm, multiplet, 2.0 H (C—CH$_2$—C); 2.60 ppm, triplet J=7.0 Hz, 2.0 H (CH$_2$—phenyl); 3.76 ppm, singlet, 3.0 H (CH$_3$—O); 4.40 ppm, triplet, J=6.3 Hz, 1.9 H (CH$_2$—O); 6.70-7.18 ppm, multiplet, 4.0 H (aromatic H).

2-phenyl-2-methyl-1-propanol nitrate (7)

Starting from 2-phenyl-2-methyl-1-propanol.
Melting point: (oil)
TLC: Rf=0.70 (petroleumether 60-80)

$^1$H-NMR(CDCl$_3$): 1.41 ppm, singlet, 6.1 H (2x CH$_3$): 4.45 ppm, singlet, 1.9 H (CH$_2$); 7.13–7.45 ppm, multiplet, 5.0 H (aromatic H).

2-(4-chlorophenyl)-2-methyl-1-propanol nitrate (8)

2-(4-chlorophenyl)-2-methyl-1-propanol (8a)

Synthesis from 2,2-dimethyl-2-(4-chlorophenyl) acetic acid in the manner as described by Nystrom R. F. and Brown W. G., J. Am. Chem. Soc. 1947; 69: 2548–9.
Melting point: 44°–48° C.
$^1$H-NMR(CDCl$_3$): 1.32 ppm, singlet, 7.0 H (2x CH$_3$+OH); 3.56 ppm, singlet, 2.0 H (CH$_2$); 7.26 ppm, singlet, 4.0 H (aromatic H).
From 8a. subsequently 8. was synthetized.
Melting point: (oil)
TLC: Rf=0.62 (diethylether:petroleumether 60–80/1:8
$^1$H-NMR(CDCl$_3$): 1.40 ppm, singlet, 6.0 H (2x CH$_3$): 4.42 ppm, singlet, 2.0 H (CH$_2$): 7.26 ppm, singlet, 4.0 H (aromatic H)

2-(1-naphthyl)ethanol nitrate (9)

Starting from 2-(1-naphtyl)ethanol
Melting point: (oil)
TLC: Rf=0.34 (diethylether:petroleumether 60–80/1:10)
$^1$H-NMR(CDCl$_3$): 3.47 ppm, triplet, J=7.0 Hz, 2.0 H (CH$_2$—naphtyl): 4.72 ppm, triplet, J=7.0 Hz, 2.0 H (CH$_2$—O); 7.26–8.10 ppm, multiplet, 7.0 H (aromatic H)

2-(2-naphthyl)-1,3-propanediol nitrate (10)

2-(2-naphtyl)-1,3-propanediol (10a)

Synthesis from the diethylester of 2-naphtylmalonic in the manner as described by Nystrom R. F. and Brown W. G., J. Am. Chem. Soc., 1947; 69; 2538–9.
Melting point: 96°–98°
$^1$H-NMR(CDCl$_3$): 2.06 ppm, singlet, 2.0 H (2x OH); 3.17 ppm, quintet, J=6.8 Hz, 0.9 H (CH); (3.92 ppm, singlet and 3.98 ppm, doublet, J=1.8 Hz) together: 4.0 H (2x CH$_2$); 7.16–7.91 ppm, multiplet, 7.1 H (aromatic H).
From 10a. subsequently 10 was synthetized.
Melting point: (oil)
TLC: Rf=0.38 (diethylether:petroleumether 60–80/1:4)
$^1$H-NMR(CDCl$_3$): 3.66 ppm, quintet, J=6.7 Hz, 0.9 H (CH); 4.81 ppm, doublet, J=6.7 Hz, 4.0 H (2x CH$_2$); 7.20–7.98 ppm, multiplet, 7.1 H (aromatic H).

1,4-bis(2-nitroxyethyl)benzene (11)

Starting from 1,4-bis(2-hydroxyethyl)benzene:
Melting point: 43°–45° C.
TLC: Rf=0.65 (diethylether:petroleumether 60–80/1:4)
$^1$H-NMR(CDCl$_3$): 3.02 ppm, triplet, J=7.0 Hz, 4.0 H (CH$_2$—groups directly bonded to phenyl ring); 4.62 ppm, triplet, J=7.0 Hz, 4.0 H (2x CH$_2$—O); 7.16 ppm, singlet, 4.0 H (aromatic H).

1,4-bis(2-nitroxyethyl)-b 2,3,5,6-tetramethylbenzene (12)

Starting from 1,4-bis(2-hydroxyethyl)-2,3,5,6-tetramethyl benzene;
Melting point: 134°–138° C.
TLC: Rf=0.80 (diethylether:petroleumether 60–80/1:5)
$^1$H-NMR(CDCl$_3$): 2.29 ppm, singlet, 12 H (4x CH$_3$); 3.03–3.30 ppm, multiplet, 4.0 H (CH$_2$-groups directly bonded to phenyl ring); 4.32–4.62 ppm, multiplet, 4.0 H (2x CH$_2$—O).

2,2-diphenylethanol nitrate (13)

Starting from 2,2-diphenylethanol.
Melting point: (oil)
TLC: Rf=0.80 (diethylether:petroleumether 60–80/1:1)
$^1$H-NMR(CDCl$_3$): 4.42 ppm, triplet, J=7.2 Hz, 1.0 H (diphenyl—CH); 5.00 ppm, doublet, 2.00 H, J=7.2 Hz (CH$_2$—O); 7.04–7.50 ppm, multiplet, 10.0 H (aromatic H).

3,3-diophenyl-1-propanol nitrate (14)

Starting from 3,3-diphenyl-1-propanol.
Melting point: (oil)
TLC: Rf=0.33 (petroleumether 60–80); Rf=0.65 (diethylether:petroleumether 60–80/1:9)
$^1$H-NMR(CDCl$_3$): 2.45 ppm, quartet, J=8.2 Hz, 2.0 H(C—CH$_2$—C); 4.06 ppm, triplet, J=8.1 Hz, 1.0 H (diphenyl—CH); 4.34 ppm, triplet, J=6.8 Hz, 2.0 H (CH$_2$—O); 7.08–7.37 ppm, multiplet, 10.0 H (aromatic H).

1,1-diphenyl-2-propanol nitrate (15)

Starting from 1,1-diphenyl-2-propanol.
Melting point: (oil)
TLC: Rf=0.67 (diethylether:petroleumether 60–80/1:6)
$^1$H-NMR(CDCl$_3$): 1.31 ppm, doublet, J=5.9 Hz, 3.0 H (CH$_3$); 4.07 ppm, deformed doublet, 1.0 H (diphenyl—CH); 5.67–6.05 ppm, multiplet, 1.0 H (CH—O); 7.26 ppm, singlet, 10.5 H (aromatic H+CHCl$_3$)

4,4-di-(4-fluorophenyl)-2-butanol nitrate (16)

1,1-di-(4-fluorophenyl)-3-butanol (16a)

Synthesis from 1,1-(4-fluorophenyl)-butan-3-one by means of sodium boron hydride in ethanol. After complete reaction of the starting material (TLC) water and dichloromethane were added to the reaction mixture. The organic layer was washed with diluted sodium hydroxide, dried over magnesium sulfate and concentrated by evaporation. The obtained compound was pure (TLC).
From 16a. subsequently 16. was synthetized.
Melting point: (oil)
TLC: Rf=0.31 (petroleumether 40–60)
$^1$H=NMR(CDCl$_3$): 1.30 ppm, doublet, J=6.1 Hz, 3.0 H (CH$_3$); 1.93–2.42 ppm, multiplet, 2.2 H (CH$_2$); 3.84–4.15 ppm, multiplet, 1.1 H (phenyl—CH); 4.56–4.95 ppm, multiplet, 1.0 H (CH—O); 6.74–7.21 ppm, multiplet, 8.0 H (aromatic H)

2-(5H-dibenzo[a,d]cycloheptene-5-yl)ethanol nitrate (17)

2-(5H-dibenzo[a,d]cycloheptene-5-yl)ethanol (17a)

Synthesis from 5H-dibenzo[a,d]cycloheptene-5-yl-acetic acid in the manner as described by Nystrom R. F. and Brown W. G., J. Am. Chem. Soc., 1947; 69: 2548–9.
Melting point: 65°–70° C.
$^1$H-NMR(CDCl$_3$): 1.35 ppm, singlet, 1.1 H (OH); 2.00 ppm, quartet, J=6.6 Hz, 1.8 H (C—CH$_2$—C); 3.34 ppm, triplet, J=6.3 Hz, 1.9 H (CH$_2$—O); 4.23 ppm, triplet, J=7.7 Hz, 1.0 H (CH); 6.88 ppm, singlet, 1.7 H (CH=CH); 7.29 ppm, singlet, 8.3 H (aromatic H).

From 17a. subsequently 17. was synthetized.
Melting point: (oil)
TLC: Rf=0.64 (diethylether:petroleumether 60-80/1:5)
$^1$H-NMR(CDCl$_3$): 2.01–2.30 ppm, multiplet, 2.0 H (C—CH$_2$—C); 3.95–4.28 ppm, multiplet, 3.0 H (CH—C—CH$_2$); 6.90 ppm, singlet, 2.0H (CH=CH; 7.27 ppm, singlet, 8.0 H (aromatic H)

2-(2-chlorothioxanthene-10-yl)ethanol nitrate (18)

2-(2-chlorothioxanthene-1-yl)ethanol (18a)

Synthesis from 2-(2-chlorothioxanthene-10-yl)acetic acid with of lithiumaluminiumhydride in dry tetrahydrofurane in the manner as described by Nystrom R. F. and Brown W. G., J. Am. Chem. Soc., 1947; 69; 2548-9
Melting point: 86°–89° C.
TLC: Rf=0.58 (dichloromethane)
$^1$H-NMR(CDCl$_3$): 1.67 ppm, singlet, 1.0 H (OH); 1.92 ppm, multiplet, 2.0 H (C—CH$_2$—C); 3.46 ppm, triplet, J=5.9 Hz, 2.0 H (CH$_2$—O); 4.24 ppm, triplet, J=7.9 Hz, 1.0 (CH); 7.00–7.48 ppm, multiplet, 7.0 H (aromatic H).

From 18a. subsequently 18. was synthetized.
Melting point: 67°–69° C.
TLC: Rf=0.84 (diethylether:petroleumether 40/1:6)
$^1$H-NMR(CDCl$_3$): 2.00–2.28 ppm, multiplet, 2.0 H (C—CH$_2$—C); 4.04–4.34 ppm, multiplet, 3.0 H (CH—C—CH$_2$); 7.95–7.25 ppm, multiplet, 7.0 H (aromatic H).

10,11-dihydro-5H-dibenzo[a,d]cycloheptene-5-ylmethanol nitrate (19)

10,11-dihydro-5H-dibenzo[a,d]cycloheptane-5ylmethanol (19a)

Sythesis from the ethyl ester of 10,11-dihydro-5H-dibenzo[a,d]cycloheptene-5-ylcarboxylic acid in the manner as described by Nystrom R. F. and Brown W. G., J. Am. Chem. Soc., 1947; 69; 2548-9.
Melting point: 55°–57° C.
$^1$H-NMR(CDCl$_3$): 1.48 ppm, singlet, 1.0 H (OH); 2.74–3.56 ppm, multiplet, 4.0 H (CH$_2$—CH$_2$); 3.94–4.34 ppm, multiplet, 3.0 H (CH—CH$_2$); 6.99–7.41 ppm, multiplet, 8.0 H (aromatic H).

From 19a. subsequently 19. was synthetized.
Melting point: (oil)
TLC: Rf=0.56 (diethylether:petroleumether 60-80/1:10)
$^1$H-NMR(CDCl$_3$): 2.76–3.61 ppm, multiplet, 4.0 H (CH$_2$—CH$_2$); 4.22–4.50 ppm, multiplet, 1.0 H (CH); 4.80–5.02 ppm, doublet, J=7.4 Hz, 1.9 H (CH$_2$—O); 7.03–7.38 ppm, multiplet, 8.0 H (aromatic H).

2-diphenylmethyl-1,3-propanediol dinitrate (20)

2-diphenylmethyl-1,3-propanediol (20a)

Synthesis from the diethylester of diphenylmethyl malonic acid in the manner as described by Nystrom R. F. and Brown W. G., J. Am. Chem. Soc., 1947; 69, 2548-9.
Melting point: 74°–78° C.
$^1$H-NMR(CDCl$_3$): 2.38–2.75 ppm, multiplet, 1.1 H (C—CH—C); 2.96 ppm, singlet, 2.2 H (2x OH); 3.33–4.22 ppm, multiplet, 5.3 H (phenyl—CH+2x CH$_2$); 6.95–7.24 ppm, multiplet, 9.2 H (aromatic H).

From 20a. subsequently 20. was synthetized.
Melting point: 81°–83° C.
TLC: Rf=0.46 (diethylether:petroleumether 60-80/1:5)
$^1$H-NMR(CDCl$_3$): 2.85–3.28 ppm, multiplet, 1.0 H (C—CH—C); 3.80–4.65 ppm, multiplet, 5.0 H (phenyl—CH+2x CH$_2$); 7.06–7.44 ppm, multiplet, 10.0 H (aromatic H).

3-phenyl-3-(4-pyridyl)-1-propanolnitrate-4-methylbenzene sulfonate (21)

3-phenyl-3-(4-pyridyl)-1-propanol (21a)

To a solution of 10 g of 4-benzylpyridine in dry tetrahydrofurane, 1 equivalent of n-butyllithium in hexane was added at −78°, followed by addition of 12.4 g of 2-bromoethoxytetrahydropyrane. Thereafter the reaction mixture was left standing overnight. Subsequently 200 ml of ethylacetate was added, the mixture was washed with water and extracted 3 times with 150 ml of 2N HCl. After standing 2 hours the aqueous layer was neutralized with sodium carbonate. After extraction with ethylacetate and drying on magnesium sulfate it was concentrated by evaporation. The residue was purified by means of column chromatography (silica gel, eluent:ethylacetate:ethanol/4:1).
Melting point: 79°–82° C.
TLC: Rf=0.49 (acetone)
$^1$H-NMR(CDCl$_3$): 2.25 ppm, quartet, J=7.1 Hz, 2.0 H (C—CH$_2$—C); 3.02 ppm, singlet, 1.0 H (OH); 3.52 ppm, triplet, J=7.1 Hz, 2—O H (CH$_2$—O); 4.14 ppm, triplet, J=7.3 Hz, 1.0 H (CH); 7.00–7.41 ppm, multiplet, 7.0 H (aromatic H); 8.39 ppm, doublet, J=5.8 Hz, 2.0 H (pyridyl-H).

From 21a. subsequently 21. was synthetized.
The nitrate ester obtained after purification by column chromatography (silica gel, eluant:dichloromethane) was dissolved in ether and 4-methylbenzenesulfonate in ether was added to said solution. The precipitate was filtered off, washed with ethylacetate and dried.
Melting point: 115°–121° C.
TLC: Rf=0.69 (ethylacetate)
$^1$H-NMR(DMSO-d$^6$): 2.29 ppm, singlet, 3-O H (CH$_3$); 2.63 ppm, quartet, J=7.2 Hz, 2.0 (C—CH$_2$—C); 4.18–4.62 ppm, multiplet, 3.0 H (CH—C—CH$_2$); 7.00–7.58 ppm, multiplet, 10.0 H (aromatic H+—SO$_3$H); 8.00 ppm, doublet, J=5.6 Hz, 2.0 H (pyridyl-H); 8.81 ppm, doublet, J=5.8 Hz, 2.0 H (pyridyl-H)

2-(3-thienyl)ethanol nitrate (22)

Starting from 2-(3-thienyl)ethanol.
Melting point: (oil)
TLC: Rf=0.75 (diethylether:petroleumether 60-80/2:5)
$^1$H-NMR(CDCl$_3$): 3.06 ppm, triplet, J=6.8 Hz, 2.0 H (thienyl-CH$_2$); 4.52 ppm, triplet, J=6.8 Hz, 2.0 H (CH$_2$); 6.86–7.38 ppm, multiplet, 3.0 H (thienyl-H).

1,3-diphenyl-2-propanol nitrate (23)

1,3-diphenyl-2-propanol (23a)

To a solution of 20 g of 1,3-diphenylacetone in 300 ml of ethanol sodium boronhydride was added with small amounts until there was not any more starting material present (TLC). The resulting solution was concentrated under reduced pressure, after which 300 ml of water was added. Said solution was subsequently extracted with diethylether. The ether extract was dried over magnesium sulfate and concentrated by evaporation.
Melting point: (oil)
TLC: Rf=0.46 (diethylether:petroleumether 60-80/2:5)

NMR(CDCl$_3$): 2.38 ppm, broad singlet, 1.0 H (OH); 2.65–2.88 ppm, multiplet, 4.0 H (2x CH$_2$); 3.82–4.20 ppm, multiplet, 1.0 H (CH); 7.04–7.43 ppm, multiplet, 10.0 H (aromatic H).

From 23a subsequently 23. was synthetized.
Melting point: (oil)
TLC: Rf=0.84 (diethylether:petroleumether 60-80/1:4)
$^1$NMR(CDCl$_3$): 2.95 ppm, doublet, J=6.5 Hz, 4.0 H (2x CH$_2$); 5.40 ppm, quintet, J=6.5 Hz, 1.0 Hz (CH); 7.01–7.44 ppm, multiplet, 10.0 H (aromatic H)

1,3-dibenzyloxy-2-propanol nitrate (24)

Starting from 1,3-dibenzyloxy-2-propanol.
Melting point: (oil)
TLC: Rf=0.54 (diethylether:petroleumether 60-80/2:5)
$^1$H-NMR(CDCl$_3$): 3.71 ppm, doublet, J=5.1 Hz, 4.0 H (CH$_2$—C—CH$_2$); 4.55 ppm, singlet, 4.0 H (2x phenyl—CH$_2$); 5.38 ppm, quintet, J=5.1 Hz, 1.0 H (CH); 7.32 ppm, singlet, 10.3 H (aromatic H).

2-diphenylmethoxyethanol nitrate (25)

Starting from 1-bromo-2-diphenylmethoxyethane and silver nitrate (method 6)
Melting point: (oil)
TLC: Rf=0.33 (diethylether:petroleumether 60-80/1:9)
NMR(CDCl$_3$): 3.60–3.82 ppm, multiplet, 2.0 1 H (CH$_2$—O—C); 4.52–4.76 ppm, multiplet, 2.0 H (CH$_2$—O—NO$_2$); 5.37 ppm, multiplet, 1.0 H (CH); 7.14–7.57 ppm, multiplet, 10.0 H (aromatic H)

2-(α-(4-chlorophenyl)-4-t.butylbenzyloxy)ethanol nitrate (26)

Starting from 1-bromo-2-(4-t.butyl-4'-chloro)-diphenyl-methoxyethane and silver nitrate (method 6).
Melting point: (oil)
TLC: Rf=0.64 (diethylether:petroleumether 60-80/1:5)
NMR(CDCl$_3$): 1.28 ppm, singlet, 9.0 H (t.butyl); 3.61–3.80 ppm, multiplet, 2.0 H (CH$_2$); 4.52–4.74 ppm, multiplet, 2.0 H (CH$_2$); 5.32 ppm, singlet, 1.0 H (CH); 7.05–7.42 ppm, multiplet, 8.0 H (aromatic H)

2-(α-(4-chlorophenyl)-4-t.butylbenzyl)-1,4:3,6-dianhydroglucitol nitrate (27)

A solution of 1.6 g of 1,4:3,6-dianhydroglucitol-5-nitrate (isosorbide-5-mononitrate), 1,6-g of 4-t.butyl-4'-chlorobenzhydrol and 0.3 g of 4-toluene sulfonic acid in 100 ml of toluene was refluxed for 2 hours in a Dean-Stark device. After cooling down the solution was washed with an aqueous sodium bicarbonate solution, dried over magnesium sulfate and concentrated by evaporation. The residue was purified by means of column chromatography (silica gel; eluant:diethylether:petroleum ether 60-80/1:1)
Melting point: (oil)
TLC: Rf=0.45 (diethylether:petroleumether 60-80/4:6)
NMR(CDCl$_3$): 1.28 ppm, singlet, 9.0 H (t.butyl); 3.68–4.27 ppm, multiplet, 5.0 H (2x CH$_2$+CH isosorbide); 4.40–4.62 ppm, multiplet, 1.0 H (CH isosorbide); 4.87–5.10 ppm, multiplet, 1.0 H (CH isosorbide); 5.18–5.47 ppm, multiplet, 2.0 H (CH benzhydryl+CH isosorbide); 7.04–7.26 ppm, multiplet, 8.0 H (aromatic H)

2-diphenylmethyl-1,4:3,6-dianhydroglucitol nitrate (28)

Synthesis identical to that described for 27. starting from 5 g of isosorbide-5-mononitrate and 5 g of diphenylmethanol.
Melting point: 93°–94° C.
TLC: Rf=0.24 (diethylether:petroleumether 60-80/45:55)
NMR(CDCl$_3$): 3.60–3.92 ppm, multiplet, 3.0 H (CH$_2$+CH isosorbide); 3.96–4.22 ppm, multiplet, 2.0 H (CH$_2$ isosorbide); 4.40–4.60 ppm, multiplet, 1.0 H (CH isosorbide); 4.83–5.08 ppm, multiplet, 1.0 H (CH isosorbide); 5.13–5.38 ppm, multiplet, 1.0 H (CH isosorbide); 5.45 ppm, singlet, 1.0 H (CH benzhydryl); 7.28 ppm, singlet, 10.0 H (aromatic H)

2-(4-chloro-α-(2-chlorothien-5-yl)benzyl)-1,4:3,6-dianhydroglucitol nitrate (29)

Synthesis identical to that described for 27. starting from 1 g of isosorbide-5-mononitrate and 1.4 g of 4-chloro-α-(2-(5-cloro)thienyl)benzylalcohol.
Melting point: (oil)
TLC (mixture of 2-disastereomers): Rf$_1$=0.54; Rf$_2$=0.48 (diethylether:petroleumether 60-80/2:1)
NMR(CDCl$_3$): 3.68–4.27 ppm, multiplet, 5.0 H (2x CH$_2$+CH isosorbide); 4.40–4.63 ppm, multiplet, 1.0 H (CH isosorbide); 4.88–5.14 ppm, multiplet, 1.0 H (CH isosorbide); 5.22–5.47 ppm, multiplet, 1.0 H (CH isosorbide); 5.55 ppm, singlet, 1.0 H (phenyl-CH); 6.51–6.84 ppm, multiplet, 1.9 H (CH—CH thienyl); 7.34 ppm, singlet, 4.0 H (phenyl H).

2-(2-thienyl)ethanol nitrate (30)

Starting from 2-(2-thienyl)ethanol.
Melting point: (oil)
TLC: Rf=0.68 (diethylether:petroleumether 60-80/1:5)
$^1$H-NMR(CDCl$_3$): 3.22 ppm, triplet, J=6.3 Hz, 2.0 H (thienyl—CH$_2$); 4.62 ppm, triplet, J=6.3 Hz, 2.0 H (CH$_2$—O); 6.64–7.32 ppm, multiplet, 3.0 H (thienyl-H).

1-phenyl-1-nitroxymethylcyclopropane (31)

Starting from 1-phenyl-1-hydroxymethylcyclopropane:
Melting point: (oil)
TLC: Rf=0.71 (diethylether:petroleumether 60-80/1:7)
$^1$H-NMR(CDCl$_3$): 1.04 ppm, singlet, 4.0 H (—CH$_2$—CH$_2$—); 4.52 ppm, singlet, 2.0 H (CH$_2$—O); 7.05–7.52 ppm, multiplet, 5.0 H (aromatic H).

3-phenoxy-1,2-propanediol dinitrate (32)

Starting from 3-phenoxy-1,2-propanediol.
Melting point: (oil)
TLC: Rf=0.64 (diethylether:petroleumether 60-80/2:1)
$^1$H-NMR(CDCl$_3$): 4.05–4.25 ppm, multiplet, 2.0 H (phenyl—O—CH$_2$); 4.52–5.1 ppm, multiplet, 2.0 H (CH$_2$—O); 5.24–5.78 ppm, multiplet, 1.0 H (>CH—); 6.68–7.48 ppm, multiplet, 5.0 H (aromatic H)

6-acetyloxy-1-hexanol nitrate (33)

Isolated from the reaction mixture for the synthesis of 1,6-hexanediol dinitrate (43).
Melting point: (oil)
TLC: Rf=0.50 (diethylether:petroleumether 60-80/1:3)

$^1$H-NMR(CDCl$_3$): 1.26-1.96 ppm, multiplet, 4.0 H (—(CH$_2$)$_4$—); 2.04 ppm, singlet, 1.0 H (—CO—CH$_3$); 4.04 ppm, triplet, J=6.3 Hz, 2.0 H (—CH$_2$—O—CO); 4.42 ppm, triplet, J=6.3 Hz, 2.0 H (—CH$_2$—O).

1,6-dihydroxybicyclo[4,4,0]decyl dinitrate (34)

Starting from 1,6-dihydroxybicyclo[4,4,0]decane.
Melting point: (oil)
TLC: mixture of 3 isomers Rf$_1$=0.95; Rf$_2$=0.86; Rf$_3$=0.70 (diethylether:petroleumether 60-80/1:1)
$^1$H-NMR(CDCl$_3$): 0.70-2.63 ppm, multiplet, 14.0 H (6x CH$_2$+2x CH); 4.20-5.16 ppm, multiplet, 2.0 H (CH—O).

1,4-cyclohexanediol dinitrate (35)

Starting from 1,4-cyclohexanediol.
Melting point: 120.9°-123.3° C.
TLC: Rf=0.6 (diethylether:petroleumether 60-80/2:1)
$^1$H-NMR(CDCl$_3$): 1.49-2.30 ppm, multiplet, 8.0 H (cyclohexyl); 4.87-5.18 ppm, multiplet, 2.0 H (2x >CH—O).

1,4-di(hydroxymethyl)cyclohexane dinitrate (36)

Starting from 1,4-di(hydroxymethyl)cyclohexane.
Melting point: 62.4°-66.5° C.
TLC: Rf=0.5 (diethylether:petroleumether 60-80/2:1)
$^1$H-NMR(CDCl$_3$): 0.90-2.12 ppm, multiplet, 10.0 H (cyclohexyl); 4.59 ppm, doublet, J=6.0 Hz, 4.0 H (2x

1,2-cyclohexanediol dinitrate (37)

Starting from 1,2-cyclohexanediol.
Melting point: (oil)
TLC: Rf=0.50 (diethylether:petroleumether 60-80/1:2)
$^1$H-NMR(CDCl$_3$); 1.16-2.42 ppm, multiplet, 8.0 H (cyclohexyl); 4.78-5.42 ppm, multiplet, 2.0 H (2 x >CH—O).

1,5-pentanediol dinitrate (38)

Starting from 1,5-pentane diol.
Melting point: (oil)
TLC: Rf=0.50 (diethylether:petroleumether 60-80/1:3)
$^1$H-NMR(CDCl$_3$): 1.28-2.00 ppm, multiplet, 6.0 H (—(CH$_2$)$_3$—); 4.46 ppm, triplet, J=6.3 Hz, 4.0 H (2x —CH$_2$—O).

1,3-cyclohexanediol dinitrate (39)

Starting from 1,3cyclohexanediol.
Melting point: (oil)
TLC: Rf=0.7 (ethylacetate:petroleumether 60-80/1:3)
$^1$H-NMR(CDCl$_3$): 1.18-2.60 ppm, multiplet, 8.0 H (cyclohexyl); 4.52-5.42 ppm, multiplet, 2.0 H (2x >CH—O).

2-hydroxy-1-cyclohexanol nitrate (40)

Starting from 1,2-cyclohexanediol.
Melting point: (oil)
TLC: Rf=0.48 (ethylacetate:petroleumether 60-80/1:3)
$^1$H-NMR(CDCl$_3$): 0.78-2.58 ppm, multiplet, 8.0 H (cyclohexyl); 3.18-3.88 ppm, multiplet, 1.0 H (>C—OH); 4.40-5.18 ppm, multiplet, 1.0 H (>CH—O)

2-ethyl-2-n.butyl-1,3-propanediol dinitrate (41)

Starting from 3,3-di(hydroxymethyl)heptane.
Melting point: (oil)
TLC: Rf=0.33 (petroleumether 60-80); Rf=0.75 (diethylether:petroleumether 60-80/1:9)
$^1$H-NMR(CDCl$_3$) 0.68-1.68 ppm, multiplet, 14.0 H (H$_3$C—CH$_2$—C—(CH$_2$)$_3$—CH$_3$); 4.29 ppm, singlet, 4.0 H 2x CH$_2$—O).

1,12-dodecanediol dinitrate (42)

Starting from 1,12-dodecanediol.
Melting point: (oil)
TLC: Rf=0.30 (petroleumether 60-80)
$^1$H-NMR(CDCl$_3$): 1.10-2.07 ppm, multiplet, 20.0 H (C—(CH$_2$)$_{10}$—C); 4.04 ppm, triplet, J=6.2 Hz, 4.0 H (2x CH$_2$—O).

1,6-hexanediol dinitrate (43)

Starting from 1,6-hexanediol.
Melting point: (oil)
TLC: Rf=0.41 (diethylether:petroleumether 60-80/1:3)
$^1$H-NMR(CDCl$_3$): 1.27-2.07 ppm, multiplet, 8.0 H (—(CH$_2$)$_4$—); 4.44 ppm, triplet, J=6.3 Hz, 4.0 H (2x —CH$_2$—O).

TABLE 1

| Tested compound | EC$_{50}$ (molar) |
|---|---|
| glyceryl trinitrate | 7.3 × 10$^{-9}$ |
| isosorbide dinitrate | 5.6 × 10$^{-7}$ |
| 1. | 1.2 × 10$^{-7}$ |
| 9. | 4.2 × 10$^{-9}$ |
| 10. | 1.3 × 10$^{-8}$ |
| 11. | 4.6 × 10$^{-9}$ |
| 12. | 7.8 × 10$^{-8}$ |
| 23. | 4.0 × 10$^{-7}$ |
| 25. | 2.5 × 10$^{-7}$ |
| 28. | 2.0 × 10$^{-7}$ |
| 37. | 3.0 × 10$^{-6}$ |
| 38. | 3.5 × 10$^{-8}$ |
| 43. | 1.9 × 10$^{-8}$ |

We claim:

1. Pharmaceutical composition having relaxing activity, for example the treatment of heart and vascular diseases which contains a nitrate ester as active substance, characterized in that said ester

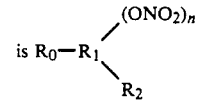

wherein
R$_0$ represents H,OH which may be esterified by substituted or unsubstituted aliphatic or (hetero)aromatic carboxylic acid, or a group

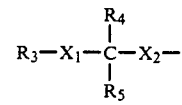

in which later formula
R$_3$ represents H or a substituted or unsubstituted (hetero)aromatic group, but is possibly lacking in case X$_2$ represents a triple bond, R₄ represents H, OH or straight or branched alkyl, alkenyl, alkynyl or alkoxy or cyclopropyl, or is identical to R₃, but is possibly lacking in case X₂ represents a triple bond, R₅ represents H or straight or branched alkyl, but is lacking in case X₂ represents a double or triple bond, X₁ represents a single bond, methylene, a substituted or unsubstituted carboxamide group or amino group, O or S, but is lacking in case X₂ represents a triple bond and X₂ represents a single bond, a double bond (in which case R₅ is then lacking), or a triple bond (in which case R₅ and either R₃—X, or R₄ are then lacking), a substituted or unsubstituted carboxamide group or amino group, O or S, R₁ represents straight or branched alkylene having 1-8 carbon atoms in a straight chain, cycloalkylene having 3-7 carbon atoms, bicycloalkylene having 5-12 carbon atoms, a 1,4:3,6-dianhydrohexitrolylene group or a derivative from said group, or mono-, di- or tri-alkylene substituted cycloalkylene, R₂ represents H, OH, straight or branched alkyl or alkylphenyl, where phenyl has the same substitution possibilities as R₃, or substituted or unsubstituted thioxanethenyl, substituted or unsubstituted benzocycloalkanyl having 5-7 carbon atoms in the cycloalkanyl chain, substituted or unsubstituted benzocycloalkenyl having 5-7 carbon atoms in the cycloalkenyl chain, substituted or unsubstituted dibenzocycloalkanyl having 5-7 carbon atoms in the cycloalkanyl chain, or substituted or unsubstituted dibenzocycloalkenyl having 5-7 carbon atoms in the cycloalkyl chain and n is 1, 2 or 3, or a salt derived from such as ester.

2. New compound, characterized

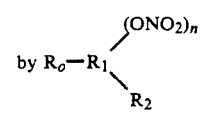

as defined in claim 1.

3. A compound according to claim 2 which is 2-(1-naphthyl)ethanol nitrate and a salt thereof.

4. A compound according to claim 2 which is 1,4-bis(2-nitroxyethyl)benzene and a salt thereof.

5. A compound according to claim 2 which is 3,3-diphenyl-1-propanol nitrate and a salt thereof.

6. A compound according to claim 2 which is 3-phenyl-3-(4-pyridyl)-1-propanol nitrate-4-methylbenzenesulfonate and a salt thereof.

7. A compound according to claim 2 which is 3-phenoxy-1,2-propanediol dinitrate and a salt thereof.

8. A compound according to claim 2 which is 1,4-di(-hydroxymethyl) cyclohexane dinitrate and a salt thereof.

9. A compound according to claim 2 which is 1,6-hexanediol dinitrate and a salt thereof.

10. A composition according to claim 1 containing, as an added ingredient, a pharmaceutically acceptable carrier.

11. A method for treating a member selected from the group consisting of ischemiatic heart diseases, decompsatio cordis, myocardial infarction, hypertension, achalasia and tardy dyskinesia which comprises administering to a subject, an effective amount of a composition according to claim 10.

* * * * *